(12) United States Patent
Hagler et al.

(10) Patent No.: US 8,177,109 B2
(45) Date of Patent: May 15, 2012

(54) METHOD AND APPARATUS FOR SUPPORT OF A MEDICAL DEVICE

(76) Inventors: Marilyn Joyce Hagler, Millville, CA (US); Richard G. Sherwood, Millville, CA (US)

(*) Notice: Subject to any disclaimer, the term of this patent is extended or adjusted under 35 U.S.C. 154(b) by 1059 days.

(21) Appl. No.: 12/018,327

(22) Filed: Jan. 23, 2008

(65) Prior Publication Data

US 2008/0173785 A1 Jul. 24, 2008

Related U.S. Application Data

(60) Provisional application No. 60/897,413, filed on Jan. 24, 2007.

(51) Int. Cl.
*A45F 5/00* (2006.01)
(52) U.S. Cl. .......................... 224/268; 224/265; 224/201
(58) Field of Classification Search ................. 224/268, 224/628, 631, 646, 650, 265, 266, 257, 258; 600/102; D3/328
See application file for complete search history.

(56) References Cited

U.S. PATENT DOCUMENTS

| | | | | | |
|---|---|---|---|---|---|
| 3,155,298 | A | * | 11/1964 | Brown | 224/268 |
| 3,809,349 | A | * | 5/1974 | Baedke | 248/51 |
| 3,862,709 | A | * | 1/1975 | Roshaven | 224/264 |
| 4,962,873 | A | * | 10/1990 | Schattel | 224/665 |
| 5,758,809 | A | * | 6/1998 | Bonner | 224/259 |
| 6,145,717 | A | * | 11/2000 | Rebeck | 224/268 |
| 6,315,179 | B1 | * | 11/2001 | Hillis | 224/268 |
| 6,329,583 | B1 | * | 12/2001 | May | 84/421 |
| 6,971,987 | B1 | * | 12/2005 | Chung | 600/102 |
| 2007/0142702 | A1 | | 6/2007 | Haller et al. | |

* cited by examiner

*Primary Examiner* — Gary Elkins
*Assistant Examiner* — Corey Skurdal
(74) *Attorney, Agent, or Firm* — Donald R. Boys; Central Coast Patent Agency

(57) ABSTRACT

A catch plate is provided for supporting the weight of a tool by a connected cable. The catch plate includes an elongate formable body with a through opening at one end for attaching the plate to a vertical surface, and a hook feature formed in the elongate body at the end opposite the through opening, the hook feature disposed at an angle away from the plane of the elongate body and formable around the connected cable.

7 Claims, 4 Drawing Sheets

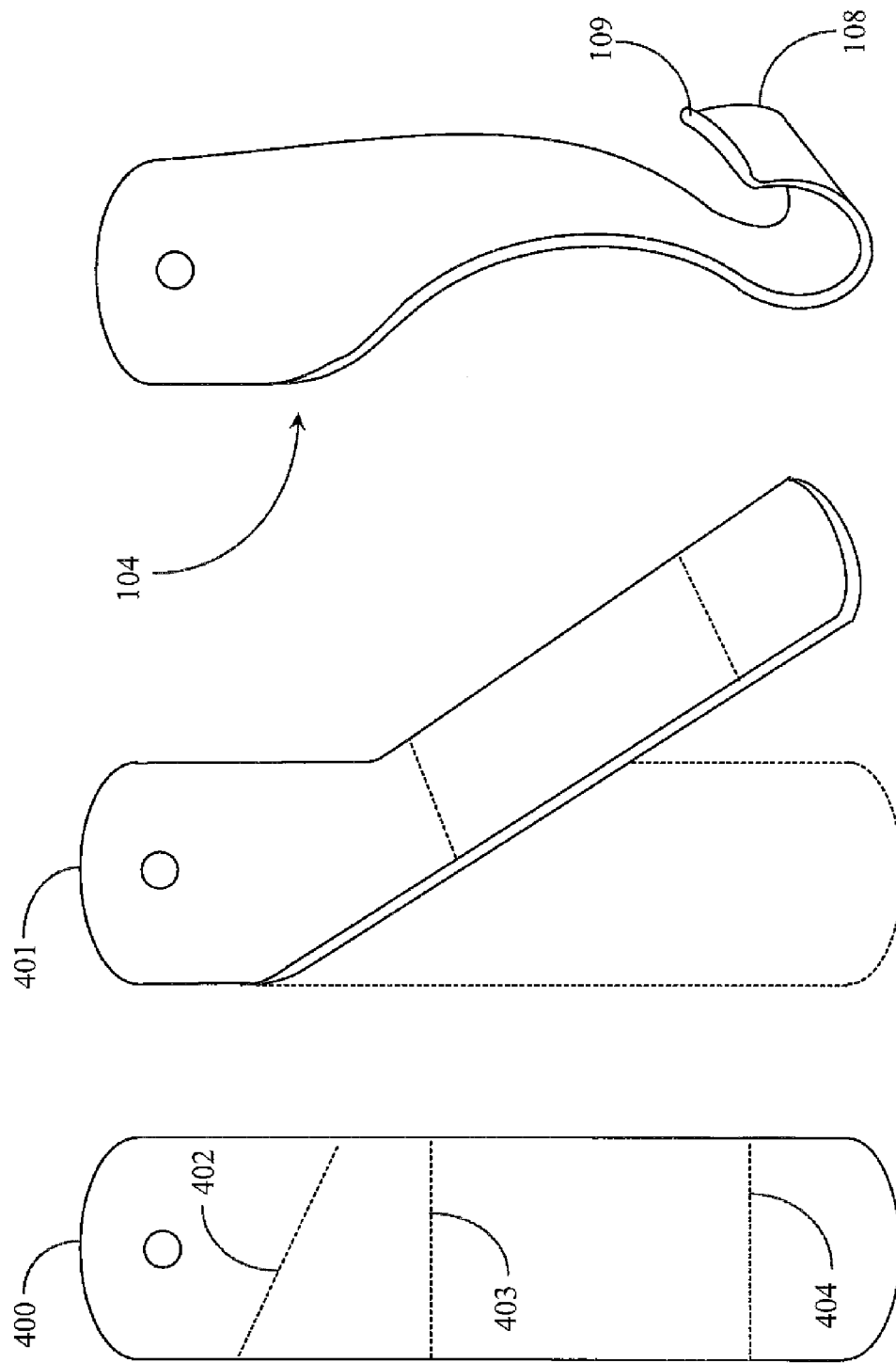

METHOD AND APPARATUS FOR SUPPORT OF A MEDICAL DEVICE

CROSS-REFERENCE TO RELATED APPLICATIONS

The present invention claims priority to a U.S. patent application Ser. No. 60/897,413 filed on Jan. 24, 2007, entitled Method and Apparatus for Providing Ergonomic Support for Repetitious Handling of a Colonoscope. The prior application is incorporated in the present application in its entirety at least by reference

BACKGROUND OF THE INVENTION

1. Field of the Invention

The present invention is in the field of medical equipment and pertains particularly to a method and apparatus for enabling ergonomic repetitious use of a colonoscope used to give colonoscopy treatments.

2. Discussion of the State of the Art

In the field of medicine, more particularly, medical treatments and procedures, there is a procedure for optically evaluating a patient's colon and for correcting any discovered problems in the colon, such as by removing polyps that may be discovered during the invasive procedure.

A piece of equipment termed a colonoscope or colonoscopic device is used to perform the procedure and remove any problem growths like polyps that might be discovered in the colon. A colonoscope is a fiber optics camera device including a cable for inserting into the colon of the patient and a hand-held control station connected, in most cases to a monitor. Doctors position a patient on his or her side and insert an optic probe into the anus and up into the colon. The probe is connected to a relatively heavy control station that includes an optic cable leading to a display station or connected monitor. The unit itself may weigh in as much as 3 to 5 pounds.

Typically, colonoscopy treatments are scheduled together in one location so as to aggregate those treatments to occur subsequently for each patient under the care of a same physician or practitioner specializing in the specific type of treatment. One challenge with this type of arrangement is that the scope itself is very heavy. A user may develop some problems handling the device such as carpal tunnel syndrome, weakness, and stiffness in the joints of the arms, muscle strains and so on over time with repetitive use. One doctor in a typical setting may perform 10 or more colonoscopies per day.

In many hospital settings there is a special room or area where all of the scheduled colonoscopies are performed. In this case it is important to get them all performed in as little time as is possible while still maintaining good patient care quality. Consequently, a doctor may perform several of these procedures in rapid succession without actually putting the unit down or taking any rest time between patients. The handle of the scoping device has a grip and includes a trigger apparatus and several pushbutton controls. The heavy portion of the system (unit) is thus held in one hand of the practitioner while the optical scooping tube is manipulated with the other hand. The image of the inside of the colon appears on a display for the practitioner to watch during the procedure.

One with skill in the art of scoping devices and methods will appreciate that repeated handling and manipulation of a heavy scoping unit like a colonoscope may cause inadvertent pain, weakness and other symptoms in the hand, arm, shoulder and wrist. Repetitive use of the device on many charges day after day can cause disabilities to develop in the practitioner rendering him or her inefficient or not able to function at all where the procedure is concerned.

Therefore, what is clearly needed in the art is a method and apparatus that solves the above problems by providing ergonomic support for a user operating a colonoscope or other heavy instrument or device. Such an apparatus and method of use may be economically provided and may increase accuracy and efficiency in the overall colonoscopy process.

SUMMARY OF THE INVENTION

According to an aspect of the present invention, a system is provided for supporting the weight of a tool by a connected cable. The system includes a vertically aligned support surface to which an attachment may be made, and a catch plate attached to the support surface. In one embodiment, the vertically aligned support surface is a vest worn by a user. In one embodiment, the tool is a colonoscope and the connected cable is a monitor cable leading from the tool to a display monitor. In another embodiment, the vertically aligned support surface is that attached to an article of clothing worn by a user.

According to another aspect of the invention, a catch plate for supporting the weight of a tool by a connected cable is provided. The catch plate includes an elongate formable body with a through opening at one end for attaching the plate to a vertical support surface, and a hook feature formed in the elongate body at the end opposite the through opening, the hook feature disposed at an angle away from the plane of the elongate body and formable around the connected cable.

In one embodiment, the elongate body is plastic and the hook feature is formed and disposed at an angle away from the plane of the elongate body by a thermal form bending process. In another embodiment, the elongate body is metallic and the hook feature is formed and disposed at an angle away from the plane of the elongate body by a sheet metal form bending process.

In one embodiment, the hook feature is smaller at its opening than at its center and is expandable to form around the connected cable. In one embodiment, the catch plate further includes a lip feature formed at the edge of the hook feature, the lip feature turned out to facilitate expansion of the hook feature around the connected cable. In one embodiment of the system, the tool is a nail gun and the connected cable is an air hose leading from the tool to an air compressor.

In yet another aspect of the invention, a method for supporting the weight of a tool by a connected cable is provided, the method using a catch plate attached to a vertical support surface, the catch plate including an elongate formable body and a hook feature formed in the elongate body the hook feature disposed at an angle away from the plane of the elongate body and formable around the connected cable comprising the steps (a) grasping the tool lifting it into position over the catch plate, (b) aligning the connected cable near its junction with the tool over the hook feature on the catch plate, (c) lowering the tool and cable pressing the cable down into the hook feature, and (d) relaxing the grasp on the tool.

In one aspect, in step (a), the tool is a colonoscope and the connected cable is a monitor cable. In another aspect, in step (a), the tool is a nail gun and the cable is an air hose. In one aspect, in step (c), the hook feature expands at its opening to accept the diameter of the cable with the aid of a lip feature formed at the end of the hook feature. In this aspect the hook feature closes around the cable after the cable passes by the opening of the hook feature. In one aspect, in step (c), the hook feature has an opening diameter larger than the cable diameter.

BRIEF DESCRIPTION OF THE DRAWING FIGURES

FIG. 4 is an elevation view of a blank used to form a catch piece according to an embodiment of the present invention.

FIG. 5 is an elevation view of the catch piece blank of FIG. 4 with a first bend.

FIG. 6 is an elevation view of a fully formed catch piece according to an embodiment of the present invention.

DETAILED DESCRIPTION

The inventor provides a method and apparatus for enabling a user to handle a colonoscope or other heavy handheld device while minimizing discomfort and muscular strain for the user that might otherwise result from repetitious use.

Figure 1:
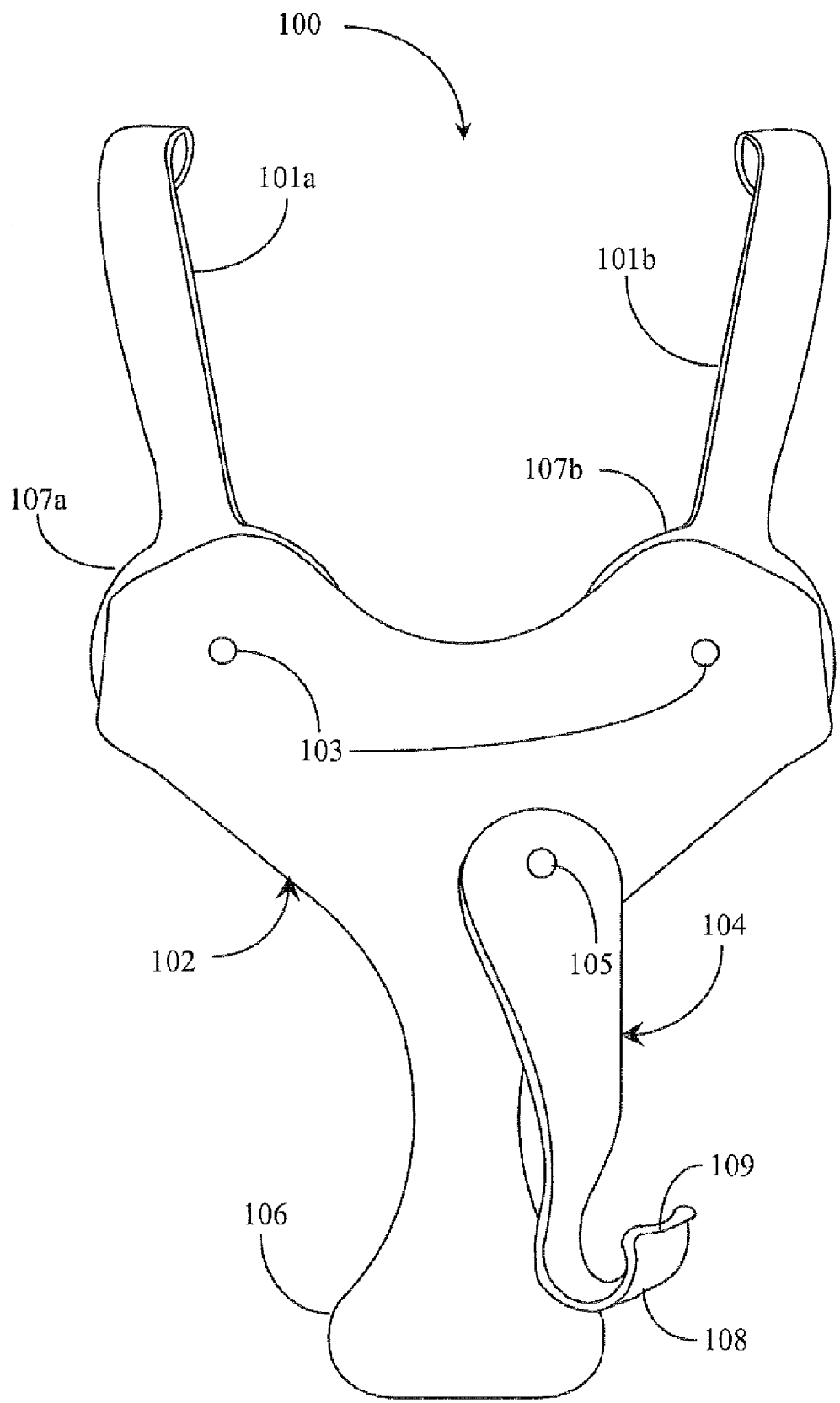
FIG. 1 is a front view of a support vest with a catch piece attached thereto according to an embodiment of the present invention.

FIG. 1 is a front view of a support vest 100 with a catch piece 104 attached thereto according to an embodiment of the present invention. Vest 100 is adapted to be worn by a user such as a doctor or other individual that would perform colonoscopies necessitating repetitious use of a colonoscope. For reference, a colonoscope is a fiber-optics camera device including a cable for inserting into the colon of a patient and a hand-held control station connected, in most cases, to a monitor. It is noted herein that the example of a doctor and colonoscope is exemplary only. The invention may be adapted for other relatively heavy hand-held devices having connections for optics, power, or compressed air.

Vest 100 has a chest plate 102 adapted to rest against a user's chest when positioned correctly. Chest plate 102 includes a lower support feature 106 integral to plate 102 adapted to provide additional support for keeping the plate vertical when worn. Chest plate 102 is generally formed in the shape of a "Y" including lower support feature 106 and left and right shoulder support features.

In one embodiment, chest plate 102 has strap holds for securing elastic or material straps (not illustrated) for the purpose of securing vest 100 more tightly against a user when worn. Straps are not essential for practice of the invention in this embodiment. In this example vest 100 further includes a shoulder piece 107a and a shoulder piece 107b. Shoulder pieces 107a and 107b may be fastened to chest plate 102 using a fastener 103 strategically located through the shoulder piece and shoulder support feature such that the position of shoulder pieces 107a and 107b is rotatably adjustable about fastener 103 on both sides of chest plate 102.

Shoulder pieces 107a and 107b support shoulder hooks 101a and 101b respectively. Shoulder hooks 101a and 101b are adapted to fit over the left and right shoulders of a user providing a way to hang vest 100 on a user so that the chest plate is properly positioned and supported against the chest of a user. Shoulder hooks 101a and 101b may be used in conjunction with straps (not illustrated) to secure vest 100 to a user. Straps are not required because the shoulder hooks are typically sufficient for the particular vest design. Cross-straps or an elastic band might be used to secure chest plate 102 to a user as required for a vest without should hooks. The exact shape of vest 100 including chest plate 102 is not particularly critical to the practice of the invention as long as proper elevation of a supported tool, in one case a colonoscope, can be achieved.

Vest 100 has a unique catch piece 104 attached to chest plate 102 in a strategic location, in this case, left of center of the chest plate. Catch plate 104 may be attached to chest plate 102 with a fastener 105. Fasteners 103 and 105 may be rivets, nut-bolt-washer combinations, or other types of fasteners. In one case shoulder pieces 107a and 107b may be adjusted by loosening fasteners 103 until the shoulder pieces may be rotated. When proper positioning is achieved the fasteners may be tightened again. Fastener 105 may enable catch plate 105 to rotate about with little or no friction. In one case, tightening fastener 105 (nut and bolt) may provide the ability to lock catch plate 105 in a specific position.

Catch piece 104 has an outward hook feature formed at the end opposite fastener 105. A lip feature 109 is provided on the upward facing edge of hook feature 108. Hook feature 108, including lip feature 109 are adapted to catch the cable apparatus of a colonoscope for example at a position just behind the hand-held control box of the device. Catch piece 104, also termed catch plate 104 has a twist provided in it so that hook feature 108 is oriented angularly, in this case to the left from the perspective of a user wearing vest 100.

In colonoscopy treatment an optics cable, also termed a camera cable, is generally manipulated with the user's right hand while the control piece of the colonoscope is generally manipulated with the left hand for a right-handed person. Catch plate 104 may be twisted in the other direction to accommodate a left-handed user if desired. In this case, catch plate 104 would be mounted to chest plate 102 right of center from the perspective of a user wearing the vest. Catch plate 104 may be manufactured from a resilient and durable polymer material or some other durable material that has resilient properties like aluminum or the like. Likewise, chest plate 102 and shoulder pieces 107a and 107b may be manufactured of aluminum with a polymer coating, or may be molded as one piece using a polymer resin material. In one case, chest plate 102, shoulder pieces 1076a and 107b and shoulder hook 101a and 101b are metallic and are overlaid in a polymer coating. In this case, a user may bend portions of vest 100 in order to obtain a better fit. However, it is noted that such features are not absolutely required in order to practice the invention.

Figure 2:
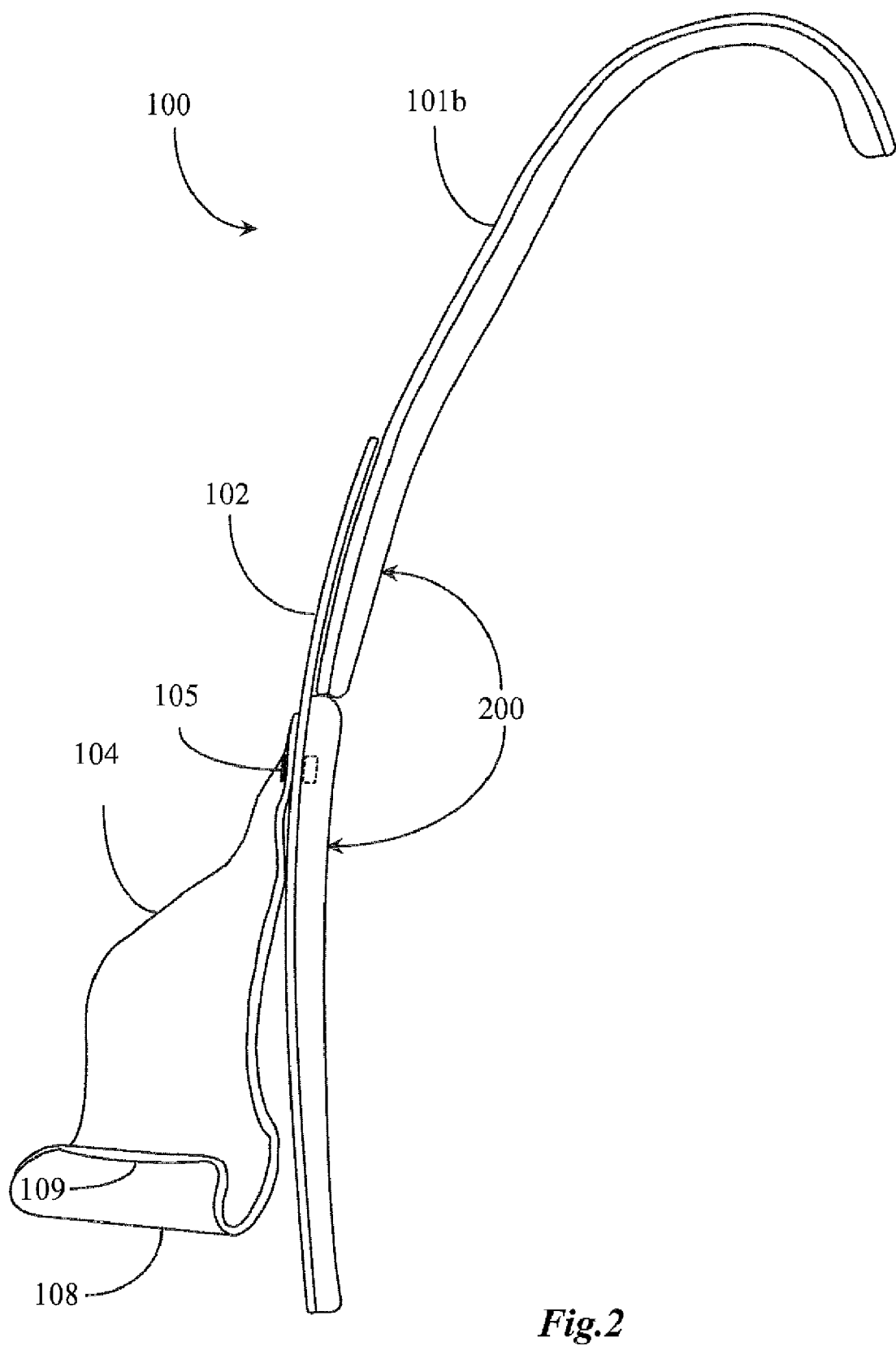
FIG. 2 is a side view of the support vest and catch piece of FIG. 1.

FIG. 2 is a side view of the support vest and catch piece of FIG. 1. In this example, vest 100 is illustrated in right-side view. In this view chest plate 102 and shoulder support pieces 107a and 107b are formed generally in a curved profile to naturally conform to the user. In this case, chest plate 102, shoulder support pieces 107a and 107b, including should hooks 101a and 101b, are backed with a polymer foam material 200 provided to make vest 100 more comfortable for wearing. The orientation of catch piece 105 is visible in this example. The amount of twist provided to catch piece 105 might be approximately 45 degrees to accomplish a desired result for orientating the tool while it is supported by the catch piece. In this example, the attached monitor cable leading from the back end of a tool such as a colonoscope to a display monitor would be supported by catch piece 104, more particularly by hook feature 108.

Figure 3:
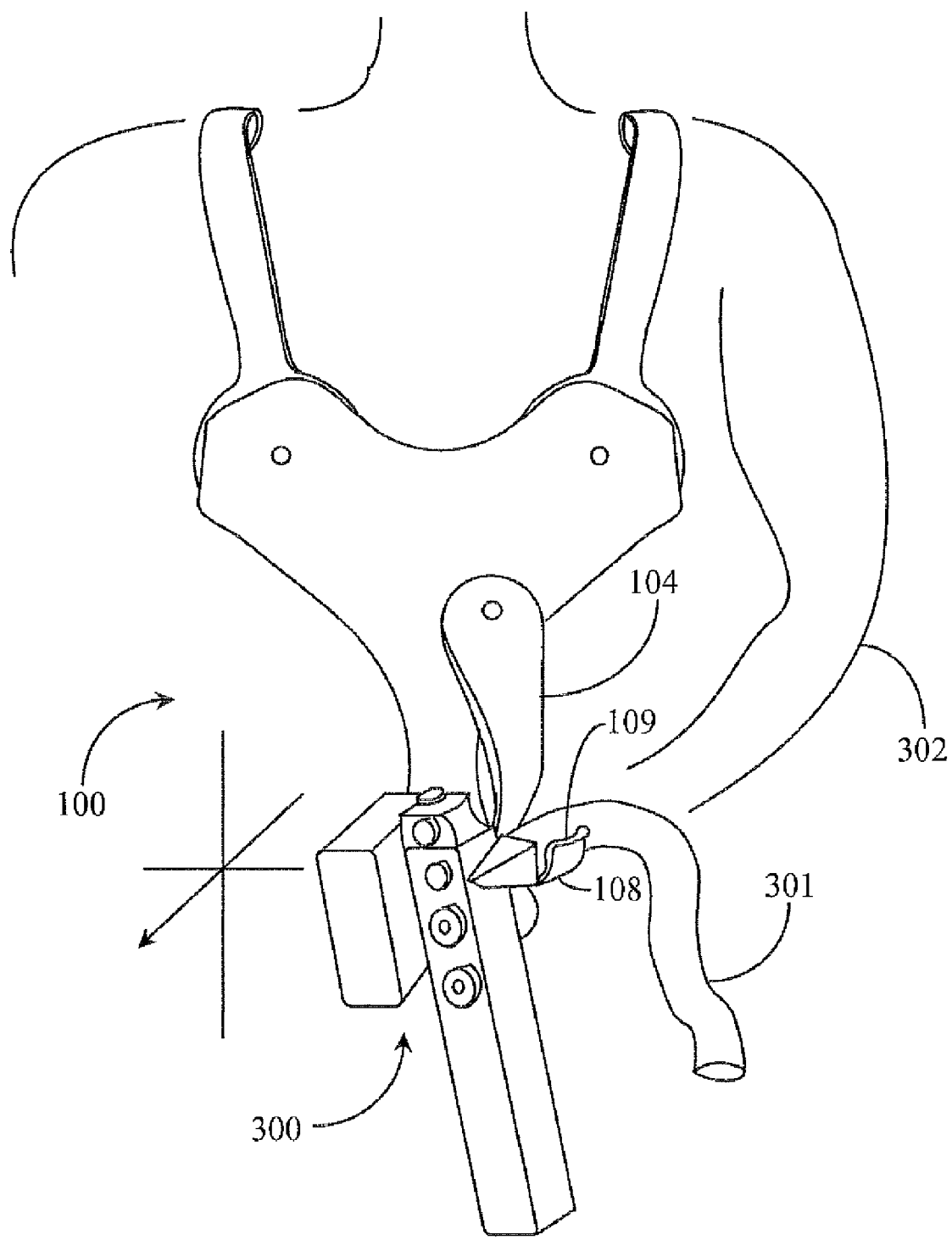
FIG. 3 is a perspective view illustrating a colonoscope supported by a catch piece according to an embodiment of the present invention.

FIG. 3 is a perspective view illustrating a colonoscope control station 300 supported by catch piece 104 of FIGS. 1 and 2 according to an embodiment of the present invention. Vest 100 is orientated relative to a user outline including left arm 302 of the user outline. Colonoscope control station 300 with monitor cable 301 is illustrated in a catch position on catch piece 104 attached to vest 100. The left hand of the user is not illustrated in this example for visibility reasons, but may be assumed to be positioned on control station 300 for manipulating required controls such as dials, buttons and the like illustrated on the station.

The catch position on cable 301 is just behind control station 300 where the cable extends from the device. Hook feature 108 is somewhat flexible and resilient and has a diameter that, in one embodiment, is just smaller than the diameter of cable 301 so that by pressing down (cable against hook feature 108 and lip 109) the hook feature opens up enough (aided by lip feature 109) to accept the cable, snapping back to its form, thereby securing device 300 to the catch piece by cable 301 and thereby supporting the weight of the device. In another embodiment, hook feature 108 may be provided with a diameter that is larger than the cable so a user may rest the device on the catch piece hook in a manner that is not restrictive. Likewise, the same effect may be achieved by simply resting the device against the catch piece hook and lip without pressing the cable into the hook. Therefore, a user has a variety of discretionary options. The weight load of device 300 is distributed across vest 100 via catch piece 104 and is no longer concentrated at the user's left arm, wrist and shoulder.

The orientation of catch piece hook feature 108 ensures that control station 300 is orientated angularly to the user's right side and angularly down in an ergonomic position of use that reduces strain on arm 302 of the user. Strain is reduced by transferring the weight of the supported device from the user's arm to the catch piece and vest. The user may operate the device, in this case, a colonoscope control station, without having to lift it out of the catch piece unless the user desires to lift it out. Other devices may also be operated while being supported by catch piece 104 such as an industrial glue gun, for example. Some devices may be required to be lifted out of the catch piece to properly operate them, but may be replaced in the catch piece in-between use so that the user does not have to continually bear the weight of the device. For example, a user trimming a long hedge may rest the trimmer on the catch piece while walking along the hedgerow.

While performing repeated colonoscopies the user may continue to wear vest 100 with catch piece 104 to support the colonoscope 300 in an ergonomic manner. It is noted herein that other devices heavy enough to produce muscular strain with continuous or repetitious use may be similarly supported by catch piece 104 without departing from the spirit and scope of the present invention. For example, an air operated impact drill may be supported on vest 100 using catch piece 104 wherein cable 301 is an air compressor hose. An electric brush trimmer with an insulated electric power cord or wire may also be supported by vest 100 and catch piece 104. There are many possibilities.

In one embodiment, multiple catch pieces 104 having different diameter hook features 108 may be provided so that they are modular to a vest like vest 100 so a user may change catch pieces appropriately for supporting devices with cable structures of different diameters. In another embodiment, one catch piece may be provided that has an adjustable hook feature diameter. The adjustment in diameter may be accomplished using a clamp oriented over the bottom of the hook feature.

In use, the left arm 302 and hand of the user may rest on top of device 300 as it is resting on catch piece 104. When using the colonoscope, the device does not have to be lifted at all. It may be operated while in place on the catch piece. For a doctor performing up to 15 colonoscopies in quick succession, i.e. patient after patient, vest 100 with catch piece 104 provides a good ergonomic solution for distributing the concentrated weight away from the left arm, hand, wrist, and shoulder of the user. Catch piece 104 also provides some assurance that a cable attached to a tool does not become dislodged while it is being used. For example, if the tool is an electric trimmer, the trimmer may be supported by catch piece 104 so that the power cord is trained away from the front other operating components of the trimmer. It is known that electric trimmers often "catch" their own power cords sometimes cutting them or damaging them.

FIG. 4 is a top view of a blank 400 used to form a catch piece 104 according to an embodiment of the present invention. Referring now to FIG. 4, catch piece 104 may be provided initially as a catch piece blank 400 with an opening provided there through for eventual fastening of the piece to a vest or other support surface. Three bend operations may be performed on blank 400, the bends performed generally along bend lines 402, 403, and 404. The first bend performed may be one that results in the desired twist angle described further above. Blank 400 may be economically provided and the bending or forming process may vary somewhat depending on the material type of the blank.

FIG. 5 is a top view of catch piece blank 400 of FIG. 4 with a first bend. Referring now to FIG. 5, blank 401 is illustrated and is equivalent to blank 400 with the first bend performed. The bend may be made by fixture in one embodiment. In another embodiment, the bend may be automated and performed by a machine.

FIG. 6 is a top view of a fully formed catch piece 104 according to an embodiment of the present invention. Referring now to FIG. 6, catch piece 104 is fully formed by completing the remaining bending operations at bend locations 403 and 404 on blank 400 of FIG. 4. The second bending operation is to form hook feature 108 and to properly orientate the hook feature by making an inward bend (along bend line 402 FIG. 4) to regain vertical orientation of the hook feature after the hook is formed. The exact order of bend operations performed is not of particular importance. The nature of the bend operations may depend in part of the choice of material. For example, if a polymer such as a thermal plastic is used then the bending may be performed under enough heat applied to the material to enable the bend. If catch piece 104 is steel or some other metal coated with polymer, then no heating is required to make the appropriate bends.

A bending fixture or fixtures may be provided to ensure repetition of the appropriate bend locations and bend radius for each bend. The lip feature may also be formed using a fixture. The lip feature is only important for enabling smooth expansion of the hook feature when pressing a cable against it. The diameter of the hook body is smaller at the lip then it is at the center of the hook feature.

In one embodiment of the present invention no vest is required. In this case, catch piece 104, may be adapted to fasten to a particularly heavy article of clothing or weight belt. A special patch with a fastening mechanism may be sewn onto such an article of clothing at the optimum position to provide maximum ergonomic relief. The catch piece could be fastened to the patch to provide enough support for most hand-held devices.

In one embodiment of the invention, a gripping substance or coating may be provided on the interfacing side of hook feature 108 of catch piece 104 to ensure that a device does not slide inadvertently forward, the cable sliding through the hook feature. Although the catch piece may easily support all of the weight of an attached tool in most embodiments, a user may have one hand on the device while it is being supported, generally the hand that will operate the tool.

It will be apparent to one with skill in the art that the tool support system and method of the invention may be provided using some or all of the mentioned features and components without departing from the spirit and scope of the present invention. It will also be apparent to the skilled artisan that the embodiments described above are exemplary of inventions that may have far greater scope than any of the singular descriptions. There may be many alterations made in the descriptions without departing from the spirit and scope of the present invention.

What is claimed is:

1. A carrier system for supporting medical device during a medical procedure, comprising:
    a substantially planar chest plate having a lower region and an upper region, the upper region of sufficient width to present a first portion of the upper region beneath an adult person's left shoulder and a second portion of the upper region below the person's right shoulder with the chest plate resting against the person's chest;
    a left shoulder piece pivotally attached to the chest plate in the first portion, the left shoulder piece extending thence upward and ending in a shoulder hook adapted to fit over the left shoulder of the person;
    a right shoulder piece pivotally attached at a position level with the attachment of the left shoulder piece to the chest plate in the second portion, the right shoulder piece extending thence upward and ending in a shoulder hook adapted to fit over the right shoulder of the person; and
    carrier cradle pivotally attached to the lower region of the chest plate, at an attachment point below the attachment of the left and right shoulder pieces, the carrier cradle comprising a descending portion extending down from the attachment point to a hook portion proceeding outward then upward from the descending portion, the descending portion twisted about a vertical axis such that the medical device, suspended in the hook portion, will be carried at an angle from the plane of the chest plate.

2. The carrier system of claim 1, wherein the medical device is a colonoscope.

3. The carrier system of claim 1 wherein the left and right shoulder pieces are each attached to the chest plate with a fastener allowing the attachment to be loosened to rotate to adjust the associated shoulder piece to the person.

4. The carrier system of claim 1 wherein the carrier cradle is attached to the chest plate with a fastener allowing the attachment to be loosened to rotate to adjust angular orientation of the carrier hook.

5. The carrier system of claim 1 further comprising a lip feature at the end of the hook providing the cradle, such that the hook must be manually urged open to insert the medical device.

6. The carrier system of claim 1 further comprising a polymer foam material backing applied to the underside of the shoulder hooks to provide a pliable surface to a user's shoulders.

7. The carrier system of claim 1 further comprising a polymer foam material backing applied to the backside of the chest plate to provide a pliable surface to a user's chest.

* * * * *